US 8,834,417 B2

(12) United States Patent
Moos et al.

(10) Patent No.: US 8,834,417 B2
(45) Date of Patent: Sep. 16, 2014

(54) NEEDLE ASSEMBLY WITH REMOVABLE DEPTH STOP

(75) Inventors: Kimberly A. Moos, Florissant, MO (US); David Rork Swisher, St. Charles, MO (US); Whitney Reynolds, Cumberland, RI (US)

(73) Assignee: Covidien AG (CH)

( * ) Notice: Subject to any disclaimer, the term of this patent is extended or adjusted under 35 U.S.C. 154(b) by 253 days.

(21) Appl. No.: 12/836,855

(22) Filed: Jul. 15, 2010

(65) Prior Publication Data

US 2010/0280410 A1    Nov. 4, 2010

Related U.S. Application Data

(62) Division of application No. 11/145,684, filed on Jun. 6, 2005, now abandoned.

(51) Int. Cl.
*A61M 5/00* (2006.01)
*A61B 10/02* (2006.01)
*A61B 19/00* (2006.01)

(52) U.S. Cl.
CPC ......... *A61B 10/025* (2013.01); *A61B 2019/306* (2013.01)
USPC ............ 604/117; 600/567; 600/566; 604/198

(58) Field of Classification Search
USPC .............. 606/180; 285/360–361; 128/202.27; 604/198, 117, 188, 192; 600/576, 600/566–567
See application file for complete search history.

(56) References Cited

U.S. PATENT DOCUMENTS

| | | | |
|---|---|---|---|
| 1,115,561 A | 11/1914 | Northey |
| 1,436,707 A | 11/1922 | Gaschke |
| 1,518,531 A | 12/1924 | Lung |
| 2,219,605 A | 10/1940 | Turkel |
| 2,854,976 A | 10/1958 | Heydrich |
| 3,539,034 A | 11/1970 | Tafeen |
| 3,610,240 A | 10/1971 | Harautuneian |
| 3,729,998 A | 5/1973 | Mueller et al. |
| 3,884,230 A | 5/1975 | Wulff |
| 3,890,971 A | 6/1975 | Leeson et al. |

(Continued)

FOREIGN PATENT DOCUMENTS

| | | |
|---|---|---|
| DE | 3805567 A1 | 8/1989 |
| EP | 1358846 A1 | 11/2003 |

(Continued)

OTHER PUBLICATIONS

Office action issued Sep. 4, 2008 in related U.S. Appl. No. 11/145,684, 11 pgs.

(Continued)

*Primary Examiner* — Mark Mashack
(74) *Attorney, Agent, or Firm* — Lisa E. Winsor, Esq.

(57) ABSTRACT

A needle assembly (10) includes a needle (14) attached to mounting structure (12), and is used to insert the needle into the body of a patient. A depth stop unit (50) of the needle assembly provides a stop surface (58) to limit the distance the needle can be inserted into the body. The depth stop unit may include a depth stop (52) that is adjustable to selectively change the depth to which the needle can be inserted. The entire depth stop unit can be removed from the needle assembly to permit the full length of the needle to penetrate into the body.

10 Claims, 9 Drawing Sheets

(56) References Cited

U.S. PATENT DOCUMENTS

| | | | |
|---|---|---|---|
| 3,893,058 | A | 7/1975 | Keith |
| 3,893,445 | A | 7/1975 | Hofsess |
| 3,904,033 | A | 9/1975 | Haerr |
| 3,915,003 | A | 10/1975 | Adams |
| 3,976,070 | A | 8/1976 | Dumont |
| 4,008,614 | A | 2/1977 | Turner et al. |
| 4,010,737 | A | 3/1977 | Vilaghy et al. |
| 4,026,287 | A | 5/1977 | Haller |
| 4,099,518 | A | 7/1978 | Baylis et al. |
| 4,112,762 | A | 9/1978 | Turner et al. |
| 4,139,009 | A | 2/1979 | Alvarez |
| 4,142,517 | A | 3/1979 | Stavropoulos et al. |
| 4,143,853 | A | 3/1979 | Abramson |
| 4,146,288 | A * | 3/1979 | Ramsay et al. ............... 439/316 |
| 4,160,450 | A | 7/1979 | Doherty |
| 4,163,446 | A | 8/1979 | Jamshidi |
| 4,177,797 | A | 12/1979 | Baylis et al. |
| 4,183,248 | A | 1/1980 | West |
| 4,211,214 | A | 7/1980 | Chikashige |
| 4,256,119 | A | 3/1981 | Gauthier |
| 4,258,713 | A | 3/1981 | Wardlaw |
| 4,258,722 | A | 3/1981 | Sessions et al. |
| 4,262,676 | A | 4/1981 | Jamshidi |
| 4,266,543 | A | 5/1981 | Blum |
| 4,266,555 | A | 5/1981 | Jamshidi |
| 4,314,565 | A | 2/1982 | Lee |
| 4,356,828 | A | 11/1982 | Jamshidi |
| 4,392,859 | A | 7/1983 | Dent |
| 4,403,617 | A | 9/1983 | Tretinyak |
| 4,425,120 | A | 1/1984 | Sampson et al. |
| 4,438,884 | A | 3/1984 | O'Brien et al. |
| 4,469,109 | A * | 9/1984 | Mehl ............................ 600/566 |
| 4,482,348 | A | 11/1984 | Dent |
| 4,487,209 | A | 12/1984 | Mehl |
| 4,513,754 | A | 4/1985 | Lee |
| 4,543,966 | A | 10/1985 | Islam et al. |
| 4,573,976 | A | 3/1986 | Sampson et al. |
| 4,613,329 | A | 9/1986 | Bodicky |
| 4,630,616 | A | 12/1986 | Tretinyak |
| 4,631,057 | A | 12/1986 | Mitchell |
| 4,639,249 | A | 1/1987 | Larson |
| 4,643,199 | A | 2/1987 | Jennings, Jr. et al. |
| 4,643,200 | A | 2/1987 | Jennings, Jr. |
| 4,655,226 | A | 4/1987 | Lee |
| 4,664,654 | A | 5/1987 | Strauss |
| 4,676,783 | A | 6/1987 | Jagger et al. |
| 4,681,567 | A | 7/1987 | Masters et al. |
| 4,693,708 | A | 9/1987 | Wanderer et al. |
| 4,695,274 | A | 9/1987 | Fox |
| 4,723,943 | A | 2/1988 | Spencer |
| 4,725,267 | A | 2/1988 | Vaillancourt |
| 4,728,320 | A | 3/1988 | Chen |
| 4,735,619 | A | 4/1988 | Sperry et al. |
| 4,737,144 | A | 4/1988 | Choksi |
| 4,738,663 | A | 4/1988 | Bogan |
| 4,743,233 | A | 5/1988 | Schneider |
| 4,747,831 | A | 5/1988 | Kulli |
| 4,747,836 | A | 5/1988 | Luther |
| 4,747,837 | A | 5/1988 | Hauck |
| 4,752,290 | A | 6/1988 | Schramm |
| 4,762,516 | A | 8/1988 | Luther et al. |
| 4,770,655 | A | 9/1988 | Haber et al. |
| 4,772,272 | A | 9/1988 | McFarland |
| 4,775,363 | A | 10/1988 | Sandsdalen |
| 4,781,684 | A | 11/1988 | Trenner |
| 4,781,692 | A | 11/1988 | Jagger et al. |
| 4,785,826 | A | 11/1988 | Ward |
| 4,790,329 | A | 12/1988 | Simon |
| 4,790,827 | A | 12/1988 | Haber et al. |
| 4,790,828 | A | 12/1988 | Dombrowski et al. |
| 4,793,363 | A | 12/1988 | Ausherman et al. |
| 4,795,432 | A | 1/1989 | Karczmer |
| 4,804,372 | A | 2/1989 | Laico et al. |
| 4,810,248 | A | 3/1989 | Masters et al. |
| 4,813,426 | A | 3/1989 | Haber et al. |
| 4,816,022 | A | 3/1989 | Poncy |
| 4,819,659 | A | 4/1989 | Sitar |
| 4,820,275 | A | 4/1989 | Haber et al. |
| 4,826,488 | A | 5/1989 | Nelson et al. |
| 4,826,490 | A | 5/1989 | Byrne et al. |
| 4,826,491 | A | 5/1989 | Schramm |
| 4,834,718 | A | 5/1989 | McDonald |
| 4,838,280 | A | 6/1989 | Haaga |
| 4,838,282 | A | 6/1989 | Strasser et al. |
| 4,842,586 | A | 6/1989 | Hogan |
| 4,846,809 | A | 7/1989 | Sims |
| 4,900,307 | A | 2/1990 | Kulli |
| 4,904,242 | A | 2/1990 | Kulli |
| 4,906,235 | A | 3/1990 | Roberts |
| 4,909,793 | A | 3/1990 | Vining et al. |
| 4,911,694 | A | 3/1990 | Dolan |
| 4,911,706 | A | 3/1990 | Levitt |
| 4,915,702 | A * | 4/1990 | Haber .......................... 604/198 |
| 4,922,602 | A | 5/1990 | Mehl |
| 4,927,414 | A | 5/1990 | Kulli |
| 4,929,241 | A | 5/1990 | Kulli |
| 4,931,044 | A | 6/1990 | Beiter |
| 4,935,013 | A | 6/1990 | Haber et al. |
| 4,943,283 | A | 7/1990 | Hogan |
| 4,944,725 | A | 7/1990 | McDonald |
| 4,950,250 | A | 8/1990 | Haber et al. |
| 4,952,207 | A | 8/1990 | Lemieux |
| 4,955,866 | A | 9/1990 | Corey |
| 4,958,625 | A | 9/1990 | Bates et al. |
| 4,960,412 | A | 10/1990 | Fink |
| 4,964,854 | A | 10/1990 | Luther |
| 4,966,587 | A | 10/1990 | Baumgart |
| 4,969,554 | A | 11/1990 | Sawaya |
| 4,978,344 | A | 12/1990 | Dombrowski et al. |
| 4,986,279 | A | 1/1991 | O'Neill |
| 5,005,585 | A | 4/1991 | Mazza |
| 5,012,818 | A | 5/1991 | Joishy |
| 5,013,304 | A | 5/1991 | Russell et al. |
| 5,031,634 | A | 7/1991 | Simon |
| 5,036,860 | A | 8/1991 | Leigh et al. |
| 5,047,044 | A | 9/1991 | Smith et al. |
| 5,049,136 | A | 9/1991 | Johnson |
| 5,051,109 | A | 9/1991 | Simon |
| 5,053,017 | A | 10/1991 | Chamuel |
| 5,057,085 | A | 10/1991 | Kopans |
| 5,059,180 | A | 10/1991 | McLees |
| 5,085,648 | A | 2/1992 | Purdy et al. |
| 5,092,851 | A | 3/1992 | Ragner |
| 5,102,394 | A | 4/1992 | Lasaitis et al. |
| 5,108,374 | A | 4/1992 | Lemieux |
| 5,109,849 | A | 5/1992 | Goodman et al. |
| 5,126,090 | A | 6/1992 | Egolf et al. |
| 5,127,916 | A | 7/1992 | Spencer et al. |
| 5,133,727 | A | 7/1992 | Bales et al. |
| 5,135,504 | A | 8/1992 | McLees |
| 5,154,703 | A | 10/1992 | Bonaldo |
| 5,171,229 | A | 12/1992 | McNeil et al. |
| 5,176,256 | A | 1/1993 | Sawaya |
| 5,183,468 | A | 2/1993 | McLees |
| 5,195,533 | A | 3/1993 | Chin et al. |
| 5,195,985 | A | 3/1993 | Hall |
| 5,213,115 | A | 5/1993 | Zytkovicz et al. |
| 5,215,525 | A | 6/1993 | Sturman |
| 5,215,528 | A | 6/1993 | Purdy et al. |
| 5,215,533 | A | 6/1993 | Robb |
| 5,217,438 | A | 6/1993 | Davis et al. |
| 5,228,451 | A | 7/1993 | Bales et al. |
| 5,256,149 | A | 10/1993 | Banik et al. |
| 5,257,632 | A | 11/1993 | Turkel et al. |
| 5,279,563 | A | 1/1994 | Brucker et al. |
| 5,279,591 | A | 1/1994 | Simon |
| 5,282,477 | A | 2/1994 | Bauer |
| 5,295,977 | A | 3/1994 | Cohen et al. |
| 5,304,136 | A | 4/1994 | Erskine et al. |
| 5,312,359 | A | 5/1994 | Wallace |
| 5,314,406 | A | 5/1994 | Arias et al. |
| 5,316,013 | A | 5/1994 | Striebel, II et al. |
| 5,320,635 | A | 6/1994 | Smith |
| 5,322,517 | A | 6/1994 | Sircom et al. |

(56) References Cited

U.S. PATENT DOCUMENTS

| | | | |
|---|---|---|---|
| 5,324,288 A | 6/1994 | Billings et al. | |
| 5,328,482 A | 7/1994 | Sircom et al. | |
| 5,331,972 A | 7/1994 | Wadhwani et al. | |
| 5,334,158 A | 8/1994 | McLees | |
| 5,338,311 A | 8/1994 | Mahurkar | |
| 5,338,314 A | 8/1994 | Ryan | |
| 5,341,816 A | 8/1994 | Allen | |
| 5,344,408 A | 9/1994 | Partika | |
| 5,348,022 A | 9/1994 | Leigh et al. | |
| 5,348,544 A | 9/1994 | Sweeney et al. | |
| 5,356,421 A | 10/1994 | Castro | |
| 5,357,974 A | 10/1994 | Baldridge | |
| 5,368,045 A | 11/1994 | Clement et al. | |
| 5,368,046 A * | 11/1994 | Scarfone et al. | 600/567 |
| 5,370,623 A | 12/1994 | Kreamer | |
| 5,385,151 A | 1/1995 | Scarfone et al. | |
| 5,385,570 A | 1/1995 | Chin et al. | |
| 5,389,104 A | 2/1995 | Hahnen et al. | |
| 5,389,106 A | 2/1995 | Tower | |
| 5,394,885 A | 3/1995 | Francese | |
| 5,395,375 A | 3/1995 | Turkel et al. | |
| 5,396,900 A | 3/1995 | Slater et al. | |
| 5,399,167 A | 3/1995 | Deniega | |
| 5,403,283 A | 4/1995 | Luther | |
| 5,405,323 A | 4/1995 | Rogers et al. | |
| 5,405,388 A | 4/1995 | Fox | |
| 5,409,461 A | 4/1995 | Steinman | |
| 5,411,486 A | 5/1995 | Zadini et al. | |
| 5,415,182 A | 5/1995 | Chin et al. | |
| 5,417,659 A | 5/1995 | Gaba | |
| 5,417,709 A | 5/1995 | Slater | |
| 5,419,766 A | 5/1995 | Chang et al. | |
| 5,421,522 A * | 6/1995 | Bowen | 239/600 |
| 5,423,766 A | 6/1995 | Di Cesare | |
| 5,425,718 A | 6/1995 | Tay et al. | |
| 5,425,884 A | 6/1995 | Botz | |
| 5,429,138 A | 7/1995 | Jamshidi | |
| 5,429,616 A | 7/1995 | Schaffer | |
| 5,454,378 A | 10/1995 | Palmer et al. | |
| 5,456,267 A | 10/1995 | Stark | |
| 5,458,658 A | 10/1995 | Sircom | |
| 5,462,062 A | 10/1995 | Rubinstein et al. | |
| 5,466,020 A * | 11/1995 | Page et al. | 285/361 |
| 5,466,223 A | 11/1995 | Bressler et al. | |
| 5,471,992 A | 12/1995 | Banik et al. | |
| 5,473,629 A | 12/1995 | Muramoto | |
| 5,476,099 A | 12/1995 | Robinson et al. | |
| 5,476,102 A | 12/1995 | Como et al. | |
| 5,478,313 A | 12/1995 | White | |
| 5,480,385 A | 1/1996 | Thorne et al. | |
| 5,482,054 A | 1/1996 | Slater et al. | |
| 5,487,734 A | 1/1996 | Thorne et al. | |
| 5,492,532 A | 2/1996 | Ryan et al. | |
| 5,501,675 A | 3/1996 | Erskine | |
| 5,507,297 A | 4/1996 | Slater et al. | |
| 5,507,298 A | 4/1996 | Schramm et al. | |
| 5,514,152 A | 5/1996 | Smith | |
| 5,522,398 A | 6/1996 | Goldenberg et al. | |
| 5,526,821 A | 6/1996 | Jamshidi | |
| 5,533,516 A | 7/1996 | Sahatjian | |
| 5,533,974 A | 7/1996 | Gaba | |
| 5,538,009 A | 7/1996 | Byrne et al. | |
| 5,542,927 A | 8/1996 | Thorne et al. | |
| 5,549,565 A | 8/1996 | Ryan et al. | |
| 5,549,708 A | 8/1996 | Thorne et al. | |
| 5,553,624 A | 9/1996 | Francese et al. | |
| 5,558,651 A | 9/1996 | Crawford et al. | |
| 5,562,629 A | 10/1996 | Haughton et al. | |
| 5,562,633 A | 10/1996 | Wozencroft | |
| 5,562,683 A | 10/1996 | Chan | |
| 5,569,299 A | 10/1996 | Dill et al. | |
| 5,570,783 A | 11/1996 | Thorne et al. | |
| 5,573,008 A | 11/1996 | Robinson et al. | |
| 5,573,510 A | 11/1996 | Isaacson | |
| 5,578,015 A | 11/1996 | Robb | |
| 5,584,809 A | 12/1996 | Gaba | |
| 5,584,810 A | 12/1996 | Brimhall | |
| 5,584,818 A | 12/1996 | Morrison | |
| 5,586,990 A | 12/1996 | Hahnen et al. | |
| 5,591,202 A | 1/1997 | Slater et al. | |
| 5,595,186 A | 1/1997 | Rubinstein et al. | |
| 5,599,310 A | 2/1997 | Bogert | |
| 5,601,585 A | 2/1997 | Banik et al. | |
| 5,601,599 A | 2/1997 | Nunez | |
| 5,615,690 A | 4/1997 | Giurtino et al. | |
| 5,623,969 A | 4/1997 | Raines | |
| 5,624,459 A | 4/1997 | Kortenbach et al. | |
| 5,630,506 A | 5/1997 | Thorne et al. | |
| 5,630,837 A | 5/1997 | Crowley | |
| 5,634,473 A | 6/1997 | Goldenberg et al. | |
| 5,643,307 A | 7/1997 | Turkel et al. | |
| 5,656,031 A | 8/1997 | Thorne et al. | |
| 5,662,610 A | 9/1997 | Sircom | |
| 5,669,883 A | 9/1997 | Scarfone et al. | |
| 5,672,161 A | 9/1997 | Allen et al. | |
| 5,679,907 A | 10/1997 | Ruck | |
| 5,685,852 A | 11/1997 | Turkel et al. | |
| 5,687,907 A | 11/1997 | Holden | |
| 5,690,619 A | 11/1997 | Erskine | |
| 5,693,022 A | 12/1997 | Haynes | |
| 5,695,467 A | 12/1997 | Miyata et al. | |
| 5,695,521 A | 12/1997 | Anderhub | |
| 5,697,904 A | 12/1997 | Raines et al. | |
| 5,697,907 A | 12/1997 | Gaba | |
| 5,700,249 A | 12/1997 | Jenkins | |
| 5,700,250 A | 12/1997 | Erskine | |
| 5,702,080 A | 12/1997 | Whittier et al. | |
| 5,702,369 A | 12/1997 | Mercereau | |
| 5,706,824 A | 1/1998 | Whittier | |
| 5,707,392 A | 1/1998 | Kortenbach | |
| 5,713,368 A | 2/1998 | Leigh | |
| 5,713,888 A | 2/1998 | Neuenfeldt et al. | |
| 5,715,832 A | 2/1998 | Koblish et al. | |
| 5,718,688 A | 2/1998 | Wozencroft | |
| 5,722,422 A | 3/1998 | Palmer et al. | |
| 5,730,150 A | 3/1998 | Peppel et al. | |
| 5,730,724 A | 3/1998 | Plishka et al. | |
| 5,735,827 A | 4/1998 | Adwers et al. | |
| 5,738,665 A | 4/1998 | Caizza et al. | |
| 5,746,753 A | 5/1998 | Sullivan et al. | |
| 5,752,923 A | 5/1998 | Terwilliger | |
| D395,609 S | 6/1998 | Knieriem et al. | |
| 5,758,655 A | 6/1998 | Como Rodriguez et al. | |
| 5,776,157 A | 7/1998 | Thorne et al. | |
| 5,795,336 A | 8/1998 | Romano et al. | |
| 5,807,275 A | 9/1998 | Jamshidi | |
| 5,807,277 A | 9/1998 | Swaim | |
| 5,810,744 A | 9/1998 | Chu et al. | |
| 5,817,069 A | 10/1998 | Arnett | |
| 5,823,970 A | 10/1998 | Terwilliger | |
| 5,823,997 A | 10/1998 | Thorne | |
| 5,824,002 A | 10/1998 | Gentelia et al. | |
| D400,808 S | 11/1998 | Schwan | |
| 5,836,917 A | 11/1998 | Thorne et al. | |
| 5,836,921 A | 11/1998 | Mahurkar | |
| 5,840,044 A | 11/1998 | Dassa et al. | |
| 5,843,001 A | 12/1998 | Goldenberg | |
| 5,848,692 A | 12/1998 | Thorne et al. | |
| 5,853,393 A | 12/1998 | Bogert | |
| 5,860,955 A | 1/1999 | Wright et al. | |
| 5,865,806 A | 2/1999 | Howell | |
| 5,871,453 A | 2/1999 | Banik et al. | |
| 5,873,886 A | 2/1999 | Larsen et al. | |
| 5,879,332 A | 3/1999 | Schwemberger et al. | |
| 5,879,337 A | 3/1999 | Kuracina et al. | |
| 5,879,338 A | 3/1999 | Mahurkar | |
| 5,882,337 A | 3/1999 | Bogert et al. | |
| 5,893,845 A | 4/1999 | Newby et al. | |
| 5,895,361 A | 4/1999 | Turturro | |
| 5,897,507 A | 4/1999 | Kortenbach et al. | |
| 5,906,594 A | 5/1999 | Scarfone et al. | |
| 5,910,130 A | 6/1999 | Caizza et al. | |
| 5,910,132 A | 6/1999 | Schultz | |
| 5,913,859 A | 6/1999 | Shapira | |

(56) References Cited

U.S. PATENT DOCUMENTS

| | | | |
|---|---|---|---|
| 5,916,175 A | 6/1999 | Bauer | |
| 5,928,163 A | 7/1999 | Roberts et al. | |
| 5,935,109 A | 8/1999 | Donnan | |
| 5,951,489 A | 9/1999 | Bauer | |
| 5,951,525 A | 9/1999 | Thorne et al. | |
| 5,951,582 A | 9/1999 | Thorne et al. | |
| 5,954,696 A | 9/1999 | Ryan | |
| 5,954,698 A | 9/1999 | Pike | |
| 5,957,887 A | 9/1999 | Osterlind et al. | |
| 5,957,892 A | 9/1999 | Thorne | |
| 5,961,526 A | 10/1999 | Chu et al. | |
| 5,964,717 A | 10/1999 | Gottlieb et al. | |
| 5,967,490 A | 10/1999 | Pike | |
| 5,976,115 A | 11/1999 | Parris et al. | |
| 5,979,840 A | 11/1999 | Hollister et al. | |
| 5,989,196 A | 11/1999 | Chu et al. | |
| 5,989,229 A | 11/1999 | Chiappetta | |
| 5,989,241 A | 11/1999 | Plishka et al. | |
| 5,993,426 A | 11/1999 | Hollister | |
| 6,000,846 A | 12/1999 | Gregory et al. | |
| 6,004,294 A | 12/1999 | Brimhall et al. | |
| 6,015,391 A | 1/2000 | Rishton et al. | |
| 6,022,324 A | 2/2000 | Skinner | |
| 6,024,727 A | 2/2000 | Thorne et al. | |
| 6,033,369 A | 3/2000 | Goldenberg | |
| 6,036,675 A | 3/2000 | Thorne et al. | |
| 6,047,729 A | 4/2000 | Hollister et al. | |
| 6,050,954 A | 4/2000 | Mittermeier | |
| 6,050,976 A | 4/2000 | Thorne et al. | |
| 6,063,037 A | 5/2000 | Mittermeier et al. | |
| 6,063,040 A | 5/2000 | Owen et al. | |
| 6,071,284 A | 6/2000 | Fox | |
| 6,080,115 A | 6/2000 | Rubinstein | |
| 6,083,176 A | 7/2000 | Terwilliger | |
| 6,083,202 A | 7/2000 | Smith | |
| 6,086,563 A | 7/2000 | Moulton et al. | |
| 6,090,078 A | 7/2000 | Erskine | |
| 6,090,108 A | 7/2000 | McBrayer et al. | |
| 6,095,967 A | 8/2000 | Black et al. | |
| 6,096,005 A | 8/2000 | Botich et al. | |
| 6,106,484 A | 8/2000 | Terwilliger | |
| 6,110,128 A | 8/2000 | Andelin et al. | |
| 6,110,129 A | 8/2000 | Terwilliger | |
| RE36,885 E | 9/2000 | Blecher et al. | |
| 6,117,108 A | 9/2000 | Woehr et al. | |
| 6,117,112 A | 9/2000 | Mahurkar | |
| 6,117,115 A | 9/2000 | Hill et al. | |
| 6,132,401 A | 10/2000 | Van Der Meyden et al. | |
| 6,135,110 A | 10/2000 | Roy | |
| 6,142,957 A | 11/2000 | Diamond et al. | |
| 6,149,629 A | 11/2000 | Wilson et al. | |
| 6,171,284 B1 | 1/2001 | Kao et al. | |
| 6,193,671 B1 | 2/2001 | Turturro et al. | |
| 6,197,007 B1 | 3/2001 | Thorne et al. | |
| 6,203,527 B1 | 3/2001 | Zadini et al. | |
| 6,210,373 B1 | 4/2001 | Allmon | |
| 6,217,556 B1 | 4/2001 | Ellingson et al. | |
| 6,221,029 B1 * | 4/2001 | Mathis et al. | 600/564 |
| 6,221,047 B1 | 4/2001 | Greene et al. | |
| 6,224,569 B1 | 5/2001 | Brimhall | |
| 6,224,576 B1 | 5/2001 | Thorne et al. | |
| 6,234,773 B1 | 5/2001 | Hill et al. | |
| 6,254,575 B1 | 7/2001 | Thorne, Jr. et al. | |
| 6,280,399 B1 | 8/2001 | Rossin et al. | |
| 6,280,401 B1 | 8/2001 | Mahurkar | |
| 6,280,419 B1 | 8/2001 | Vojtasek | |
| 6,280,420 B1 | 8/2001 | Ferguson et al. | |
| D448,314 S | 9/2001 | Chen | |
| 6,283,925 B1 | 9/2001 | Terwilliger | |
| 6,287,278 B1 | 9/2001 | Woehr et al. | |
| 6,293,700 B1 | 9/2001 | Lund et al. | |
| 6,302,852 B1 | 10/2001 | Fleming, III et al. | |
| 6,309,376 B1 | 10/2001 | Alesi | |
| 6,312,394 B1 | 11/2001 | Fleming, III | |
| 6,315,737 B1 | 11/2001 | Skinner | |
| 6,321,782 B1 | 11/2001 | Hollister | |
| 6,322,537 B1 | 11/2001 | Chang | |
| 6,334,857 B1 | 1/2002 | Hollister et al. | |
| 6,340,351 B1 | 1/2002 | Goldenberg | |
| 6,358,265 B1 | 3/2002 | Thorne, Jr. et al. | |
| 6,361,525 B2 | 3/2002 | Capes et al. | |
| 6,379,333 B1 | 4/2002 | Brimhall et al. | |
| 6,379,338 B1 | 4/2002 | Garvin | |
| 6,383,144 B1 | 5/2002 | Mooney et al. | |
| 6,406,459 B1 | 6/2002 | Allmon | |
| 6,409,701 B1 | 6/2002 | Cohn et al. | |
| 6,416,484 B1 | 7/2002 | Miller et al. | |
| 6,443,910 B1 | 9/2002 | Krueger et al. | |
| 6,443,927 B1 | 9/2002 | Cook | |
| 6,478,751 B1 | 11/2002 | Krueger et al. | |
| 6,485,473 B1 | 11/2002 | Lynn | |
| 6,488,663 B1 | 12/2002 | Steg | |
| 6,501,384 B2 | 12/2002 | Chapman et al. | |
| 6,517,516 B1 | 2/2003 | Caizza | |
| 6,519,569 B1 | 2/2003 | White et al. | |
| 6,520,938 B1 | 2/2003 | Funderburk et al. | |
| 6,537,255 B1 | 3/2003 | Raines | |
| 6,537,259 B1 | 3/2003 | Niermann | |
| 6,551,328 B2 | 4/2003 | Kortenbach | |
| 6,554,778 B1 | 4/2003 | Fleming, III | |
| 6,569,125 B2 | 5/2003 | Jepson et al. | |
| 6,575,919 B1 | 6/2003 | Reiley et al. | |
| 6,582,402 B1 | 6/2003 | Erskine | |
| 6,582,446 B1 | 6/2003 | Marchosky | |
| 6,585,704 B2 | 7/2003 | Luther et al. | |
| 6,592,556 B1 | 7/2003 | Thorne | |
| 6,595,954 B1 | 7/2003 | Luther et al. | |
| 6,595,955 B2 | 7/2003 | Ferguson et al. | |
| 6,613,018 B2 | 9/2003 | Bagga et al. | |
| 6,616,604 B1 | 9/2003 | Bass et al. | |
| 6,616,630 B1 | 9/2003 | Woehr et al. | |
| 6,623,458 B2 | 9/2003 | Woehr et al. | |
| 6,626,850 B1 | 9/2003 | Chau et al. | |
| D480,977 S | 10/2003 | Wawro et al. | |
| 6,629,959 B2 | 10/2003 | Kuracina et al. | |
| 6,635,003 B2 | 10/2003 | Marchant | |
| 6,638,252 B2 | 10/2003 | Moulton et al. | |
| 6,638,254 B2 | 10/2003 | Nakagami | |
| 6,652,486 B2 | 11/2003 | Bialecki et al. | |
| 6,652,490 B2 | 11/2003 | Howell | |
| 6,663,592 B2 | 12/2003 | Rhad et al. | |
| 6,673,047 B2 | 1/2004 | Crawford et al. | |
| 6,673,060 B1 | 1/2004 | Fleming, III | |
| 6,682,510 B2 | 1/2004 | Niermann | |
| 6,689,102 B2 | 2/2004 | Greene | |
| 6,692,471 B2 | 2/2004 | Boudreaux | |
| 6,698,921 B2 | 3/2004 | Siefert | |
| 6,699,221 B2 | 3/2004 | Vaillancourt | |
| 6,702,786 B2 | 3/2004 | Olovson | |
| 6,709,419 B2 | 3/2004 | Woehr | |
| 6,719,732 B2 | 4/2004 | Courteix | |
| 6,723,075 B2 | 4/2004 | Davey et al. | |
| 6,727,805 B2 | 4/2004 | Hollister et al. | |
| 6,730,043 B2 | 5/2004 | Krueger et al. | |
| 6,731,216 B2 | 5/2004 | Ho et al. | |
| 6,749,576 B2 | 6/2004 | Bauer | |
| 6,749,588 B2 | 6/2004 | Howell et al. | |
| 6,749,595 B1 | 6/2004 | Murphy | |
| 6,755,793 B2 | 6/2004 | Lamoureux et al. | |
| 6,761,704 B2 | 7/2004 | Crawford | |
| 6,761,706 B2 | 7/2004 | Vaillancourt | |
| 6,764,567 B2 | 7/2004 | Sperko et al. | |
| 6,767,336 B1 | 7/2004 | Kaplan | |
| 6,770,050 B2 | 8/2004 | Epstein | |
| 6,796,962 B2 | 9/2004 | Ferguson et al. | |
| 6,798,348 B1 | 9/2004 | Wilker et al. | |
| 6,811,308 B2 | 11/2004 | Chapman et al. | |
| 6,821,267 B2 | 11/2004 | Veillon, Jr. et al. | |
| 6,827,488 B2 | 12/2004 | Knieriem et al. | |
| 6,832,992 B2 | 12/2004 | Wilkinson | |
| 6,839,651 B2 | 1/2005 | Lantz et al. | |
| 6,846,314 B2 | 1/2005 | Shapira | |
| 6,849,051 B2 | 2/2005 | Sramek et al. | |
| 6,855,128 B2 | 2/2005 | Swenson | |

(56) References Cited

U.S. PATENT DOCUMENTS

| | | |
|---|---|---|
| 6,855,130 B2 | 2/2005 | Saulenas et al. |
| 6,875,183 B2 | 4/2005 | Cervi |
| 6,890,308 B2 | 5/2005 | Islam |
| 6,902,546 B2 | 6/2005 | Ferguson |
| 6,916,292 B2 | 7/2005 | Morawski et al. |
| 6,916,314 B2 | 7/2005 | Schneider et al. |
| 6,923,813 B2 | 8/2005 | Phillips et al. |
| 6,936,036 B2 | 8/2005 | Wilkinson et al. |
| D512,506 S | 12/2005 | Layne et al. |
| D512,924 S | 12/2005 | Ikeda |
| 6,981,948 B2 | 1/2006 | Pellegrino et al. |
| 6,983,062 B2 | 1/2006 | Smith |
| 6,984,213 B2 | 1/2006 | Horner et al. |
| 6,984,216 B2 | 1/2006 | Sendijarevic et al. |
| 6,989,003 B2 | 1/2006 | Wing et al. |
| 7,001,363 B2 | 2/2006 | Ferguson et al. |
| 7,004,927 B2 | 2/2006 | Ferguson et al. |
| 7,018,343 B2 | 3/2006 | Plishka |
| 7,021,824 B2 | 4/2006 | Yamada et al. |
| 7,033,324 B2 | 4/2006 | Giusti et al. |
| 7,036,984 B2 | 5/2006 | Penney et al. |
| 7,063,703 B2 | 6/2006 | Reo |
| 7,108,679 B2 | 9/2006 | Alchas |
| 7,112,191 B2 | 9/2006 | Daga |
| 7,118,552 B2 | 10/2006 | Shaw et al. |
| 7,147,607 B2 | 12/2006 | Wang |
| 7,179,244 B2 | 2/2007 | Smith et al. |
| 7,204,812 B2 | 4/2007 | Wang |
| 7,207,973 B2 | 4/2007 | Barrelle |
| 7,226,434 B2 | 6/2007 | Carlyon et al. |
| 7,238,169 B2 | 7/2007 | Takagi et al. |
| 7,247,148 B2 | 7/2007 | Murashita |
| 7,300,420 B2 | 11/2007 | Doyle |
| 7,341,573 B2 | 3/2008 | Ferguson et al. |
| 7,377,908 B2 | 5/2008 | Buetikofer et al. |
| 7,413,562 B2 | 8/2008 | Ferguson et al. |
| 7,458,954 B2 | 12/2008 | Ferguson et al. |
| 7,481,466 B2 * | 1/2009 | Horimoto et al. ............. 285/376 |
| 7,488,306 B2 | 2/2009 | Nguyen |
| 7,500,965 B2 | 3/2009 | Menzi et al. |
| 7,513,888 B2 | 4/2009 | Sircom et al. |
| 7,517,348 B2 | 4/2009 | Vetter et al. |
| 7,530,965 B2 | 5/2009 | Villa et al. |
| 7,601,139 B2 | 10/2009 | Woehr et al. |
| 7,641,620 B2 | 1/2010 | Wingler |
| 7,662,108 B2 | 2/2010 | Dunker et al. |
| 7,798,993 B2 | 9/2010 | Lim et al. |
| 2003/0114797 A1 * | 6/2003 | Vaillancourt et al. ......... 604/171 |
| 2003/0176810 A1 | 9/2003 | Maahs et al. |
| 2003/0220617 A1 | 11/2003 | Dickerson |
| 2004/0071182 A1 | 4/2004 | Quinn et al. |
| 2004/0077973 A1 * | 4/2004 | Groenke et al. ............. 600/567 |
| 2004/0153005 A1 | 8/2004 | Krueger |
| 2004/0236288 A1 | 11/2004 | Howell et al. |
| 2005/0023825 A1 * | 2/2005 | Nakamura et al. ............. 285/81 |
| 2005/0027263 A1 | 2/2005 | Woehr et al. |
| 2005/0054987 A1 | 3/2005 | Perez et al. |
| 2005/0070850 A1 | 3/2005 | Albrecht |
| 2005/0070851 A1 | 3/2005 | Thompson et al. |
| 2005/0075609 A1 | 4/2005 | Latona |
| 2005/0113716 A1 | 5/2005 | Mueller, Jr. et al. |
| 2005/0131345 A1 | 6/2005 | Miller |
| 2005/0165404 A1 | 7/2005 | Miller |
| 2005/0192536 A1 | 9/2005 | Takagi et al. |
| 2005/0267383 A1 | 12/2005 | Groenke et al. |
| 2005/0273057 A1 | 12/2005 | Popov |
| 2005/0277845 A1 | 12/2005 | Cooke et al. |
| 2006/0064101 A1 | 3/2006 | Arramon |
| 2006/0116603 A1 | 6/2006 | Shibazaki et al. |
| 2006/0189936 A1 | 8/2006 | Carlyon et al. |
| 2006/0200195 A1 | 9/2006 | Yang |
| 2006/0276772 A1 | 12/2006 | Moos et al. |

FOREIGN PATENT DOCUMENTS

| | | |
|---|---|---|
| JP | 6241914 A | 9/1994 |
| WO | 9622800 A1 | 8/1996 |
| WO | 9742989 A1 | 11/1997 |
| WO | 2004060138 | 7/2004 |
| WO | 2004091687 A2 | 10/2004 |
| WO | 2005009246 | 2/2005 |
| WO | 2005053774 A1 | 6/2005 |
| WO | 2005060679 A2 | 7/2005 |

OTHER PUBLICATIONS

Response filed Dec. 29, 2008 to Office Action dated Sep. 4, 2008 from related U.S. Appl. No. 11/145,684, 10 pgs.

Office action issued Mar. 24, 2009 in related U.S. Appl. No. 11/145,684, 7 pgs.

Response filed Jun. 1, 2009 to Office Action dated Mar. 24, 2009 from related U.S. Appl. No. 11/145,684, 7 pgs.

Office action issued Aug. 28, 2009 in related U.S. Appl. No. 11/145,684, 8 pgs.

Response filed Nov. 20, 2009 to Office Action dated Aug. 28, 2009 from related U.S. Appl. No. 11/145,684, 7 pgs.

Office action issued Feb. 2, 2010 in related U.S. Appl. No. 11/145,684, 7 pgs.

* cited by examiner

NEEDLE ASSEMBLY WITH REMOVABLE DEPTH STOP

RELATED APPLICATION

This application is a divisional application under 35 U.S.C. 121 and claims the benefit to pending U.S. patent application Ser. No. 11/145,684 filed Jun. 6, 2005, entitled NEEDLE ASSMEBLY WITH REMOVABLE DEPTH STOP, which is incorporated herein by reference in its entirety for all purposes.

CROSS REFERENCE TO RELATED APPLICATION

This application includes subject matter in common with co-assigned U.S. patent application Ser. No. 11/146,173, entitled Bayonet Release of Safety Shield for Needle Tip, filed Jun. 6, 2005, and published as U.S. 2006-0276772. The subject matter of this application is incorporated herein in its entirety by reference for all purposes.

BACKGROUND OF THE INVENTION

This invention relates generally to needles used in medicine and more particularly to a needle assembly having a depth stop to limit penetration of the needle into the subject, which depth stop can be selectively removed from the needle.

In some medical applications needles are used to make relatively deep penetrations into the body in order to perform their tasks. For instance where it is necessary to obtain a biopsy sample, the needle may have to penetrate deep inside tissue to the location from which the sample is to be taken. However, there are also situations where the needle has to penetrate a substantial distance through tissue in order to inject a drug or withdraw fluid. One specific example is that of accessing the intramedullary canal of bone. This may be done to collect a specimen of bone marrow or fluid from the intramedullary canal. It is also possible that a drug or other fluid may be infused into the canal through the needle.

To penetrate the hard cortical bone surrounding the intramedullary canal, the needle must be hard and strong, and substantial force has to be applied to the needle. The needle is typically mounted on a handle that can be grasped by a medical technician to supply the necessary force to penetrate the cortical bone to reach the intramedullary canal. It is important that the medical technician exercise care so that the needle is not driven elsewhere in the body other than the target bone. Depending upon the location of the bone selected for penetration, the bone may be near to organs or blood vessels that could be damaged by a misdirected needle. For example, if the needle penetrates too deeply, it could damage an untargeted area of the body. Thus, the use of a bone needle assembly of this type requires the simultaneous exercise of substantial force and precision.

One way to reduce the chance that the needle will damage the body is to provide a depth stop that limits the depth of penetration of the needle into the body. Typically the depth stop is disposed around the needle below the handle and can engage the exterior of the body to stop the inward thrust of the needle. The depth stop reduces the length of the needle that is available for penetrating into the body. The appropriate depth of penetration can vary widely from one patient to the next. For example, an obese patient may require penetration of several inches of skin and soft tissue to reach the bone, while a thin patient requires very little penetration to reach the bone. Moreover, the location of the target bone may call for a different depth of penetration. To meet this need, depth stop units have been provided that permit the depth stop to be adjusted to expose a greater or lesser length of the needle for penetration into the body. While these adjustable depth stop units provide greater flexibility they do not fully meet the need for variability in needle length. Moreover, some procedures have less reason to use the depth stop than others. Medical technicians differ on their preference for use of needle assemblies incorporating depth stops.

In instances where a depth stop is present in the needle assembly, a substantial length of the needle will never be available for use to penetrate into the body because it will remain covered by the depth stop. This is true even if the depth stop is adjusted to expose the maximum possible length of the needle for penetration. Accordingly, it is necessary to keep on hand multiple needle assemblies having different lengths and/or needle assemblies that do not have depth stops.

SUMMARY OF THE INVENTION

In one aspect of the present invention, a convertible needle assembly generally comprises a mounting structure and a needle having a longitudinal axis and a sharp end, the needle being mounted on the mounting structure and projecting outwardly from the mounting structure so that the sharp end is generally remote from the mounting structure. A depth stop adapted to limit the depth of penetration of the needle is releasably connected by a rotary connector to the needle assembly. The released depth stop is removable from the needle for increasing the possible depth of penetration of the needle.

In another aspect of the present invention, a bone needle assembly generally comprises a handle and a needle having a longitudinal axis and a sharp end. The needle is mounted on the handle at a location away from the sharp end of the needle and projects outwardly from the handle. A depth stop unit comprises a positioning stem and a depth stop mounted on the position stem and movable along a length of the stem to different selected positions along the stem and along the longitudinal axis of the needle. The depth stop has a stop surface adapted to limit the depth of penetration of the needle. A rotary connector of the depth stop unit is adapted to releasably connect the stem to the needle assembly. The rotary connector is capable of releasing connection of the stem so that the stem and depth stop may be removed from the needle for increasing the possible depth of penetration of the needle.

In still another aspect of the present invention, a method of adjusting a permissible depth of penetration of a needle of a needle assembly generally comprises releasing a rotary connection of a depth stop unit to the needle assembly. The depth stop unit includes a depth stop positioned along a longitudinal axis of the needle and limiting the depth of penetration of the needle to a first depth. The depth stop unit is slid off of the needle to expose an additional length of the needle for penetration of the needle to a second depth greater than the first depth.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
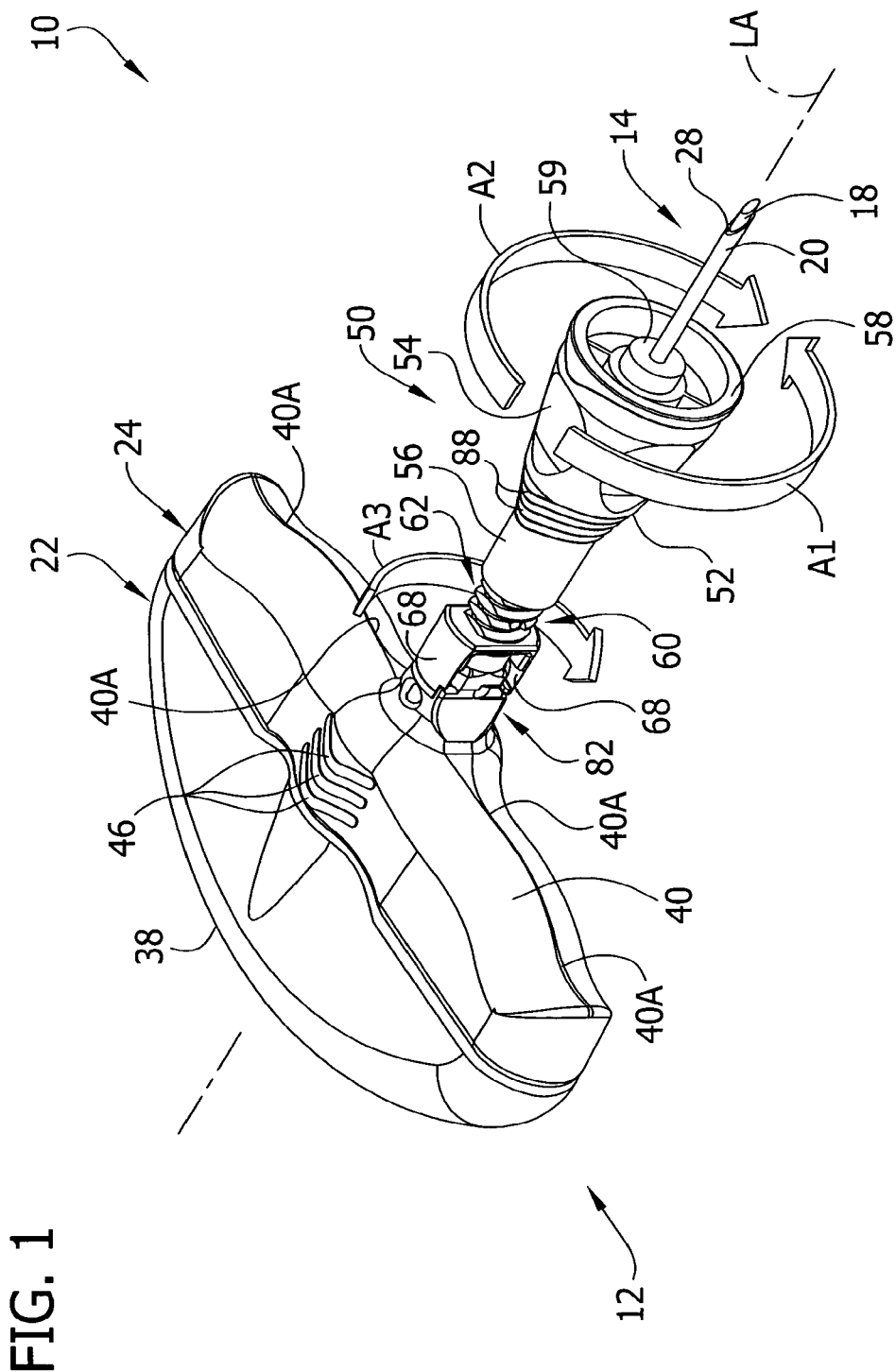
FIG. 1 is a perspective of a bone needle assembly.
Figure 2:
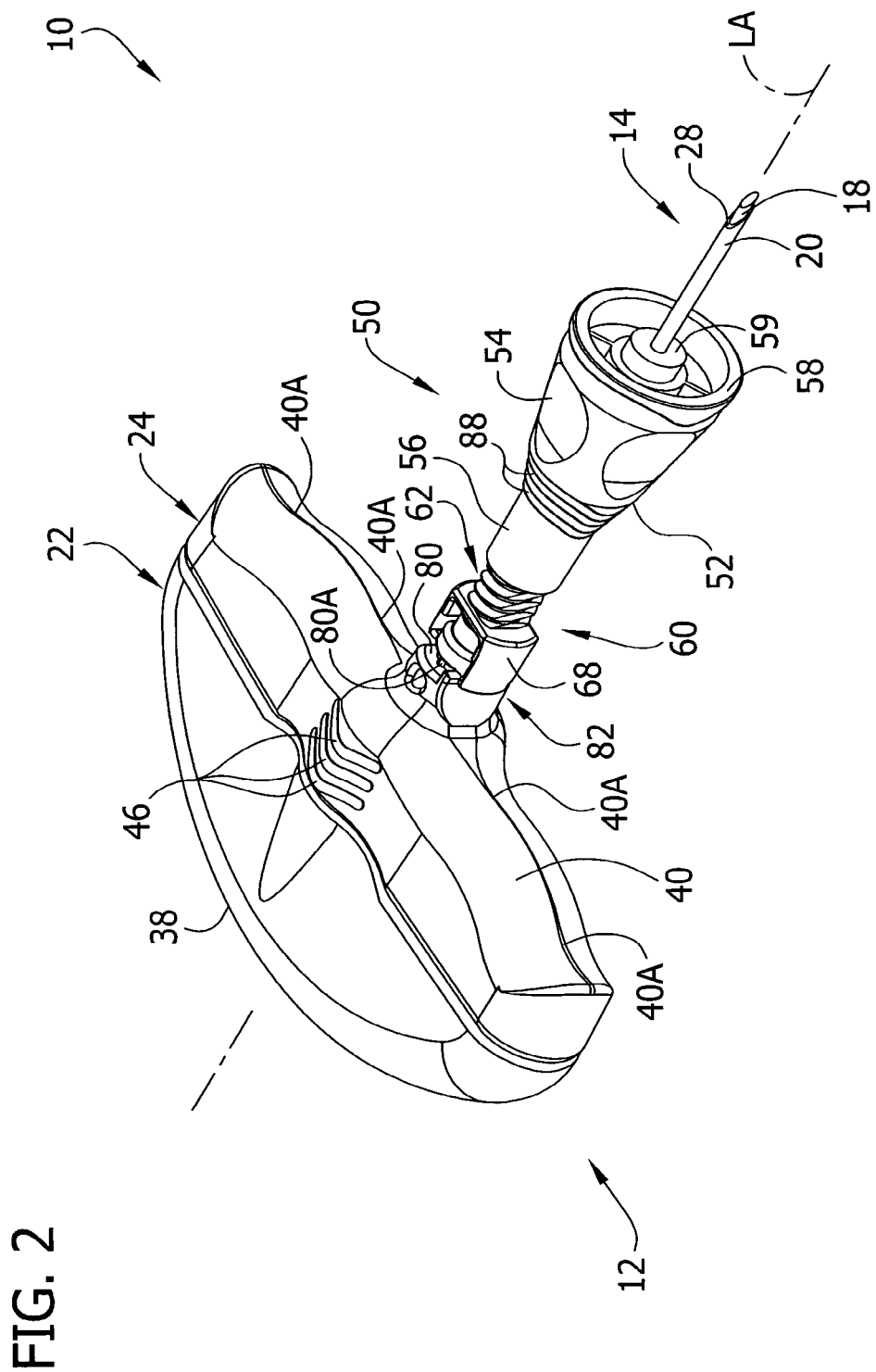
FIG. 2 is the perspective of FIG. 1 with a depth stop unit released from connection to the assembly.
Figure 3:
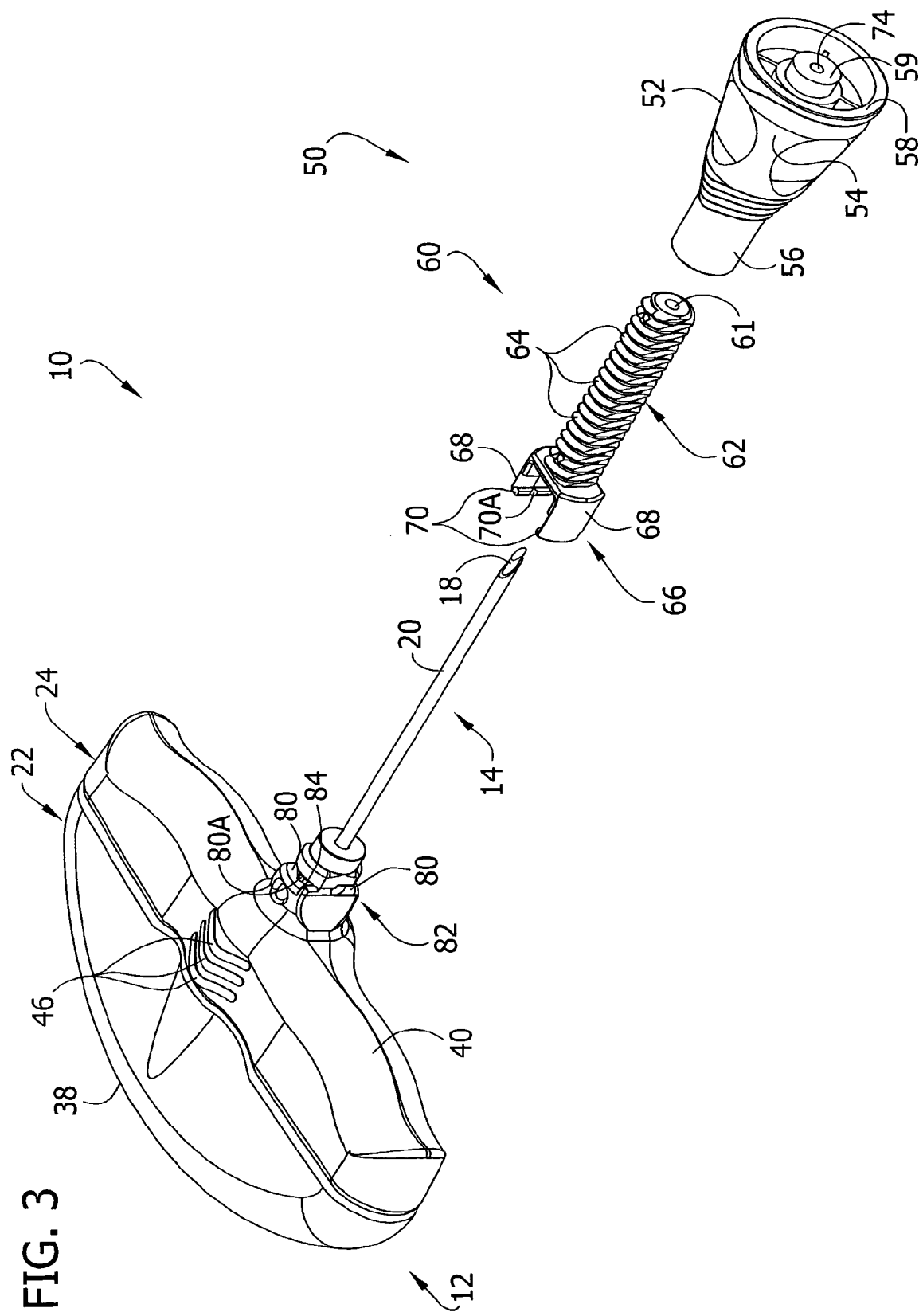
FIG. 3 is the perspective of FIG. 2 with a depth stop unit moved off the needed assembly and exploded.

Referring now to the drawings and in particular to FIGS. 1-3, a bone needle assembly constructed according to the principles of the present invention is indicated generally at 10. The bone needle assembly includes a handle 12 (broadly, "mounting structure"), and a needle 14, all reference numbers indicating their subjects generally. The needle 14 includes a stylet 18 and a cannula 20 that can receive the stylet. The handle 12 includes a first or proximal handle member (indicated generally at 22) mounting the stylet 18, and a second or distal handle member (indicated generally at 24) mounting the cannula 20. "Proximal" and "distal" refer to the relative location of the handle members to a medical technician when the needle assembly is in use. The proximal handle member 22 is in contact with the palm of the technician's hand in use, and the distal handle member 24 is on the opposite side of the proximal handle member from the palm. It will be understood that a needle could include only a single component part, or more than two parts within the scope of the present invention. Similarly, a handle could be a single part or more than two parts. Moreover, the present invention has application to needle assemblies other than bone needle assemblies, and other than to needle assemblies having a depth stop. It is envisioned that the present invention also has use outside the field of needles.

The cannula 20 has an axial passage extending the length of the cannula and opening at both ends of the cannula. A distal tip 28 of the cannula 20 is beveled and sharpened. A proximal end portion of the cannula 20 is received in the distal handle member 24. The stylet 18 is solid and includes a sharp distal tip 32, and a proximal end portion received in the proximal handle member 22. The stylet 18 can be inserted through the axial passage opening in the proximal end portion of the cannula 20 and received entirely through the axial passage of the cannula so that its sharp distal tip 32 projects axially outward from the distal tip 28 of the cannula. The stylet 18 provides the tool for penetrating the cortical bone, and can be removed from the cannula 20 once the intramedullary canal is accessed by the needle 14.

The handle 12 formed by the proximal and distal handle members 22, 24 has an ergonomic shape that can be comfortably received in a medical technician's hand, and allows the technician to easily control the needle assembly 10 as he or she applies the substantial forces needed to penetrate the bone. More specifically, the top or proximal surface 38 of the proximal handle member 22 is rounded in conformance with the shape of the palm of the hand. The bottom or distal surface 40 of the distal handle member 24 is also rounded but is undulating in shape thereby forming finger wells 40A for receiving the technician's fingers. The proximal and distal handle members 22, 24 can be securely connected together when the stylet 18 is received in the cannula 20, so that the handle 12 acts essentially as a single piece when used to drive the needle 14 through a patient's skin and into the bone. The proximal and distal handle members 22, 24 can be disconnected and moved apart for removing the stylet 18 from the cannula 20.

To assemble the proximal handle member 22 and stylet 18 with the distal handle member 24 and cannula 20, the sharp distal tip 32 of the stylet is inserted into the central open portion of the distal handle member so that it enters the axial passage of the cannula. The proximal and distal handle members are turned from their aligned position to a position in which the proximal handle member 22 is perpendicular to the distal handle member 24 (not shown). When the handle members 22, 24 are fully brought together, they are turned toward alignment with each other. This results in the handle members 22, 24 being interconnected in the position illustrated in FIGS. 1 and 2. Thereafter, it will require nearly a 90 degree turn of the proximal handle member 22 relative to the distal handle member 24 to disconnect these components. Accordingly, accidental separation of the handle members 22, 24 in use is resisted. Wavy ribs 46 on the distal handle member 24 are provided for gripping the distal handle member to disconnect and separate the distal handle member from the proximal handle member 22. The wave shape of the ribs 46 suggests to the medical technician (because the ribs extend both around a longitudinal axis LA of the needle and along the needle axis) that first twisting and then axial movement is needed to achieve separation of the proximal handle member 22 and stylet 18 from the distal handle member 24 and cannula 20.

The proximal end portion of the stylet 18 extends into the open center of the proximal handle member 22, and is secured is a suitable manner to the proximal handle member. For instance, the handle member 22 may be molded around the stylet 18 or the stylet may be attached to the proximal handle member by an adhesive. The proximal handle member 22 can be formed of polymeric or other material. Although shown as opaque in the drawings, the handle member 22 could be partially or totally transparent. A proximal end portion of the cannula 20 extends into a tubular, projecting portion 66 of the distal handle member 24 located at its center. The cannula 20 is mounted on the distal handle member 24 in a suitable manner. For instance, the distal handle member 24 may be molded around the cannula 20 or the cannula may be adhered to the distal handle member. The distal handle member 24 can be formed of polymeric or other suitable material. Although shown as opaque, the handle member 24 could be partially or totally transparent.

The needle assembly 10 further comprises a depth stop unit (broadly, "an operative member), generally indicated at 50. The depth stop unit includes a depth stop 52 that has a generally conical portion 54 with a cylindrical nose 56 projecting therefrom, calling to mind roughly the shape of a space capsule. The conical portion 54 has an annular bottom stop surface 58 that is engageable with the body of the patient to limit the penetration depth of the needle 14 into the body. A hub 59 generally in the center of the bottom of the depth stop 52 is sized and shaped to receive and hold a tube (not shown) by a releasable interference fit. The tube covers the sharp ends 28, 32 of the cannula 20 and stylet 32, and is removed by pulling off of the hub 59 prior to usage of the needle assembly 10.

Figure 5:
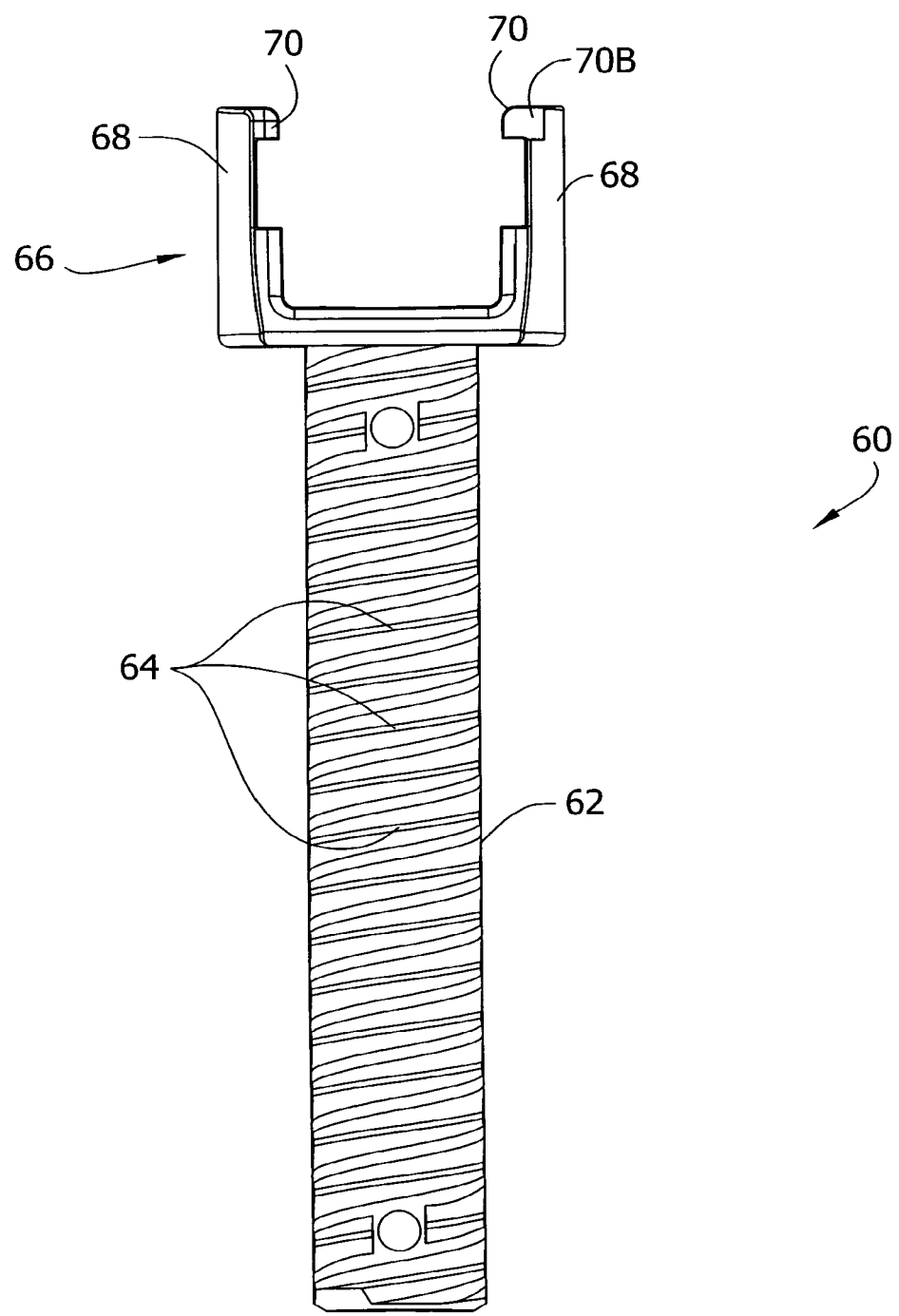
FIG. 5 is an elevation of a threaded member of the depth stop unit.
Figure 6:
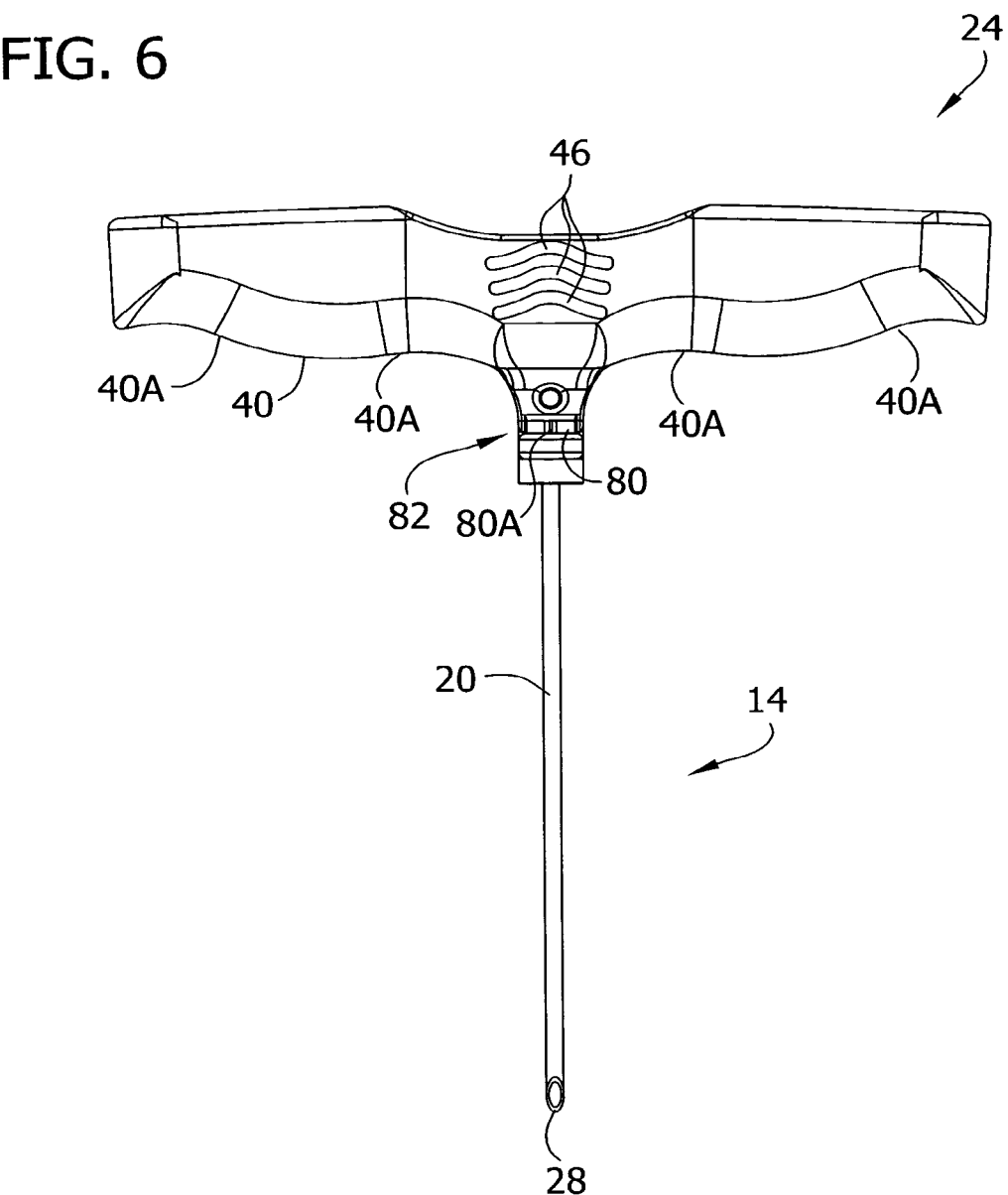
FIG. 6 is a front elevation of a distal handle member of the needle assembly.

The depth stop unit 50 further includes an elongate, tubular threaded member, indicated generally at 60, on which the depth stop 52 is threadably mounted. The threaded member 60 has an axially extending passage 61 (FIG. 3) that extends completely through the length of the threaded member. The passage 61 receives the needle 14 through the threaded member 60. Referring to FIG. 5, the threaded member 60 includes a positioning stem 62 having threads 64. A connector (indicated generally at 66) of the threaded member 60 comprises two arms 68 projecting upward from the positioning stem and having radially inwardly projecting fingers 70 at their free ends. The arms 68 are located on diametrically opposite sides of the threaded member 60. The connector 66 can releasably attach the threaded member 60 and depth stop 52 to the distal handle member 24, as will be described more fully hereinafter. Although the positioning stem 62 and connector 66 are shown as one piece, a connector could be formed separate from the positioning stem. Moreover, the positioning stem 62 could be eliminated and the connector 66 could directly attach the depth stop 52 to the distal handle member 24 without departing from the scope of the present invention.

Figure 4:
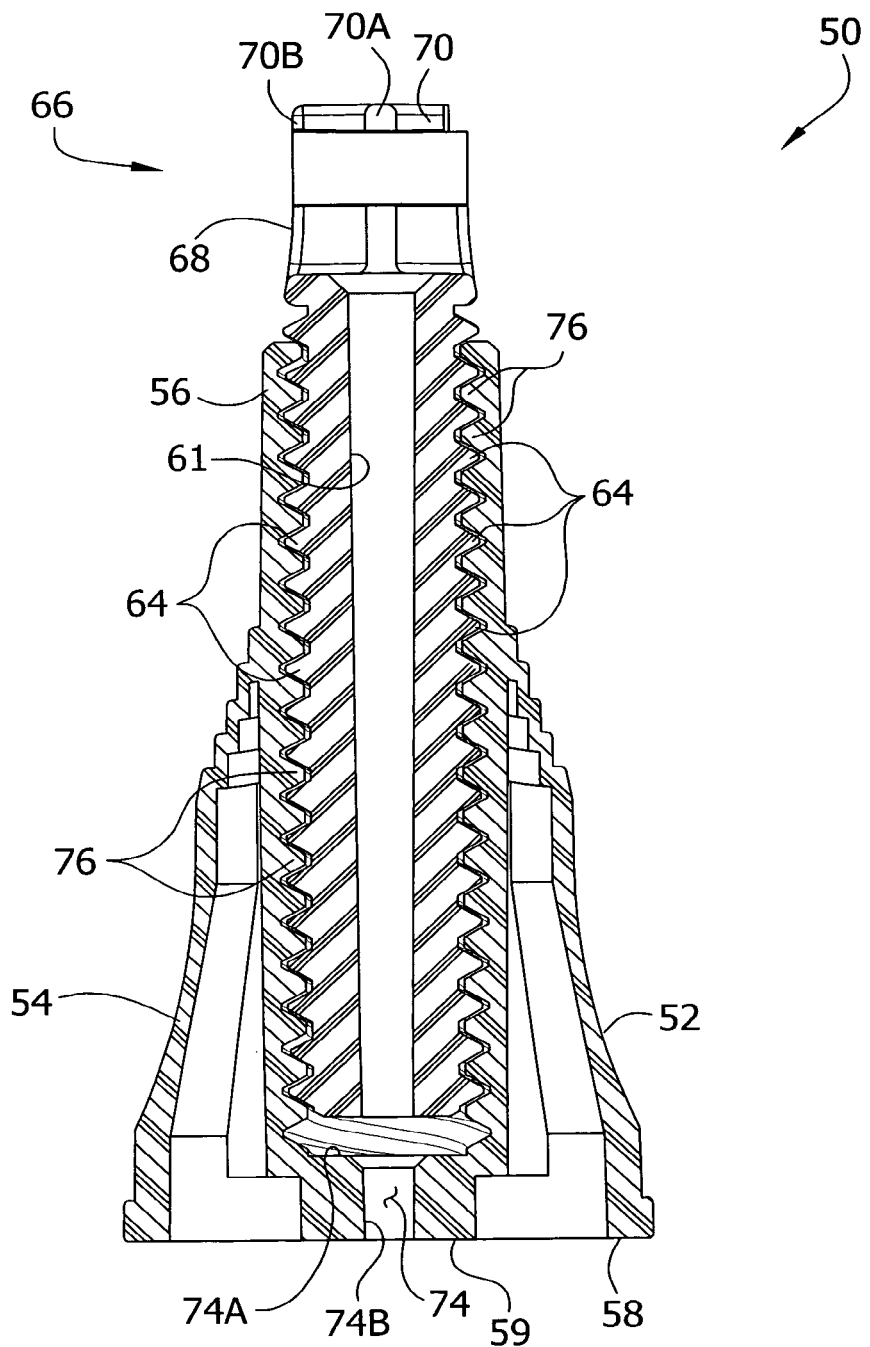
FIG. 4 is a longitudinal section of the depth stop unit.

As shown in FIG. 4, the depth stop 52 has an axially extending passage 74 extending through the entire length of the depth stop and including a larger diameter portion 74A and a smaller diameter portion 74B at its bottom end (as oriented in FIG. 4). The larger diameter portion 74A receives the positioning stem 62 of the threaded member 60 into the depth stop. The smaller diameter portion 74B allows the needle 14 to pass out of the depth stop 52. The larger diameter portion 74A has threads 76 that mate with the threads 64 of the positioning stem 62. Rotation of the depth stop 52 about a longitudinal axis of the threaded member 60 (which generally coincides with the longitudinal axis LA of the needle 14) in the direction indicated by arrow A1 in FIG. 1 causes the depth stop to move relative to the positioning stem 62 toward a distal end of the threaded member. Rotation of the depth stop 52 on the positioning stem 62 in the opposite direction indicated by arrow A3 in FIG. 1 causes the depth stop to move toward the proximal end of the threaded member 60. Movement toward the distal end of the threaded member 60 has the effect of shortening the length of the needle 14 located between sharpened distal tips 28, 32 of the cannula 20 and stylet 18 and the stop surface 58 of the depth stop 52. The possible depth of penetration of the needle 14 into the body is therefore reduced. Moving the depth stop 52 toward the proximal end of the threaded member 60 increases the length of the needle 14 located between the sharpened tips 28, 32 and the stop surface 58 of the depth stop 52. The possible depth of penetration of the needle 14 into the body is therefore increased. Thus by rotating the depth stop 52 on the positioning stem 62, a particular limited depth of penetration of the needle 14 into the body of the patient can be selected. Among other things, this can prevent the needle 14 overshooting its target bone and inadvertently damaging another area inside the body.

The adjustment of the depth stop 52 along the length of the threaded member 60 allows considerable variance in the effective length of the needle 14 and selected depth of penetration. However, in some instances it will be necessary or desirable to employ substantially the full length of the needle 14 projecting outward from the tubular portion 66 of the distal handle member 24 to reach the target bone. The depth stop unit 50 can be removed from the needle assembly 10 by disconnecting the threaded member 60 from the distal handle member 24.

Figure 7:
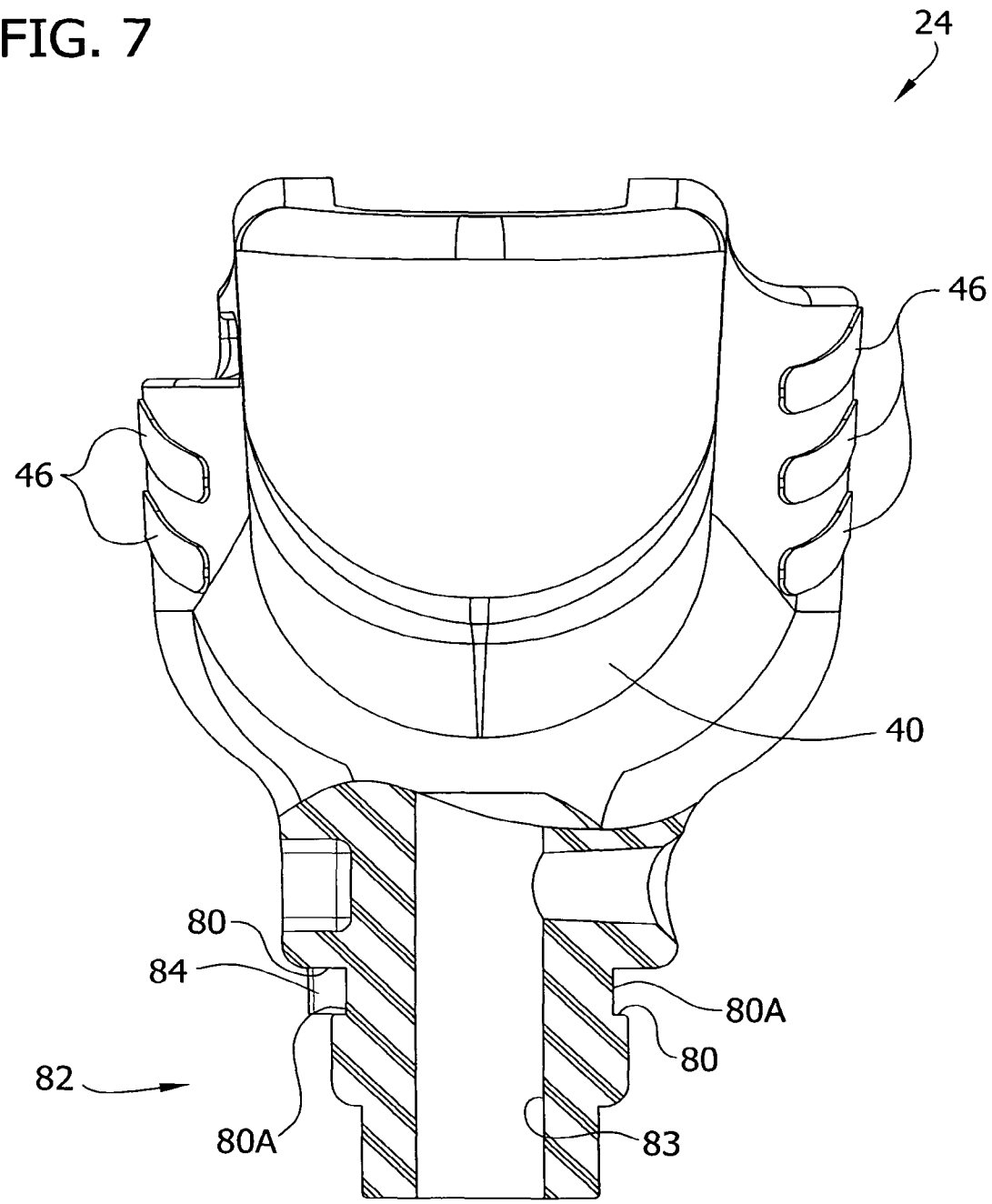
FIG. 7 is a left side elevation of the distal handle member with a portion of the distal handle member broken away and a cannula of the needle assembly removed.
Figure 8:
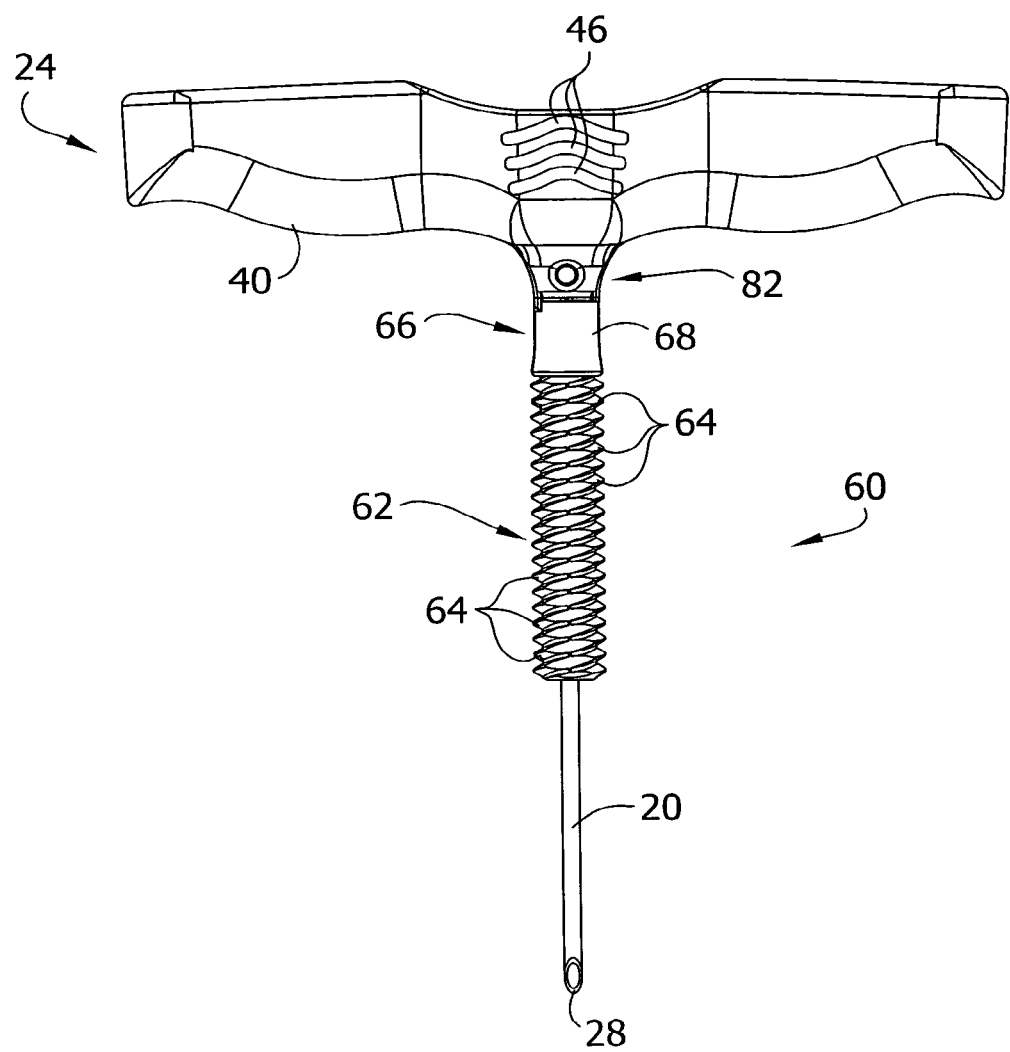
FIG. 8 is a front elevation of the distal handle member with the threaded member connected thereto.
Figure 9:
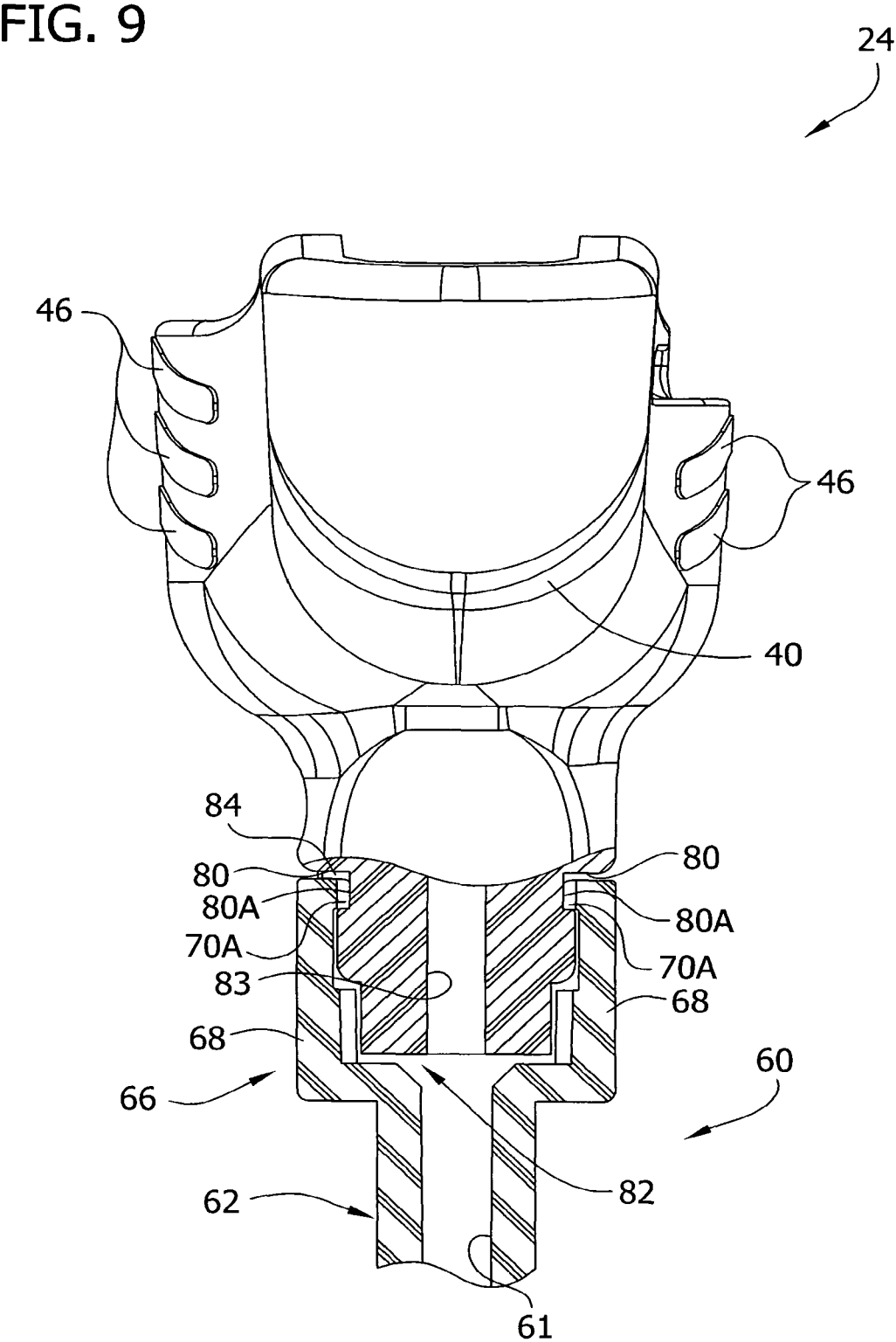
FIG. 9 is a right side elevation of the distal handle member of FIG. 8 with a portion of the handle member broken away and the cannula removed.

The threaded member 60 is attached to the distal handle member 24 by the fingers 70 of the arms 68 being received in circumferentially extending slots 80 formed in a projecting tubular portion (generally indicated at 82) of the distal handle member (see, FIGS. 7 and 9). The tubular portion 82 includes a hole 83 that receives the cannula 20 (removed in FIGS. 7 and 9) and allows for passage of the stylet 18 into the cannula. A threaded member or depth stop could be attached at other locations on a needle assembly without departing from the scope of the present invention. The slots 80 each are open on one circumferential end of the slot and include an end wall 84 on the other end of the slot. The end wall 84 locates the fingers 70 and positions the threaded member 60 relative to the handle 12. The fingers 70 and slots 80 are shaped for retaining the fingers in the slots thereby to prevent inadvertent disconnection of the threaded member from the distal handle member 24. More specifically, each of the fingers 70 has a triangular recess 70A located generally in the center of the finger. Each slot 80 has a corresponding triangular projection 80A in the center of the slot.

When the triangular projections 70A are received in the triangular recesses 80A, the threaded member 60 is held against rotation relative to the tubular portion 82 of the distal handle member 24 (FIGS. 1 and 9). Thus, the threaded member 60 is prevented from inadvertent disconnection from the distal handle member 24. By applying sufficient force, the interlocked connection of the triangular recesses 70A and triangular projections 80A can be overcome to release the threaded member 60 from the distal handle member 24. To connect the threaded member 60 to the distal handle member 24, the threaded member is rotated in a direction opposite arrow A3 from its FIG. 2 position back to its FIG. 1 position. A tapered leading edge portion 70B of each finger 70 first enters its respective slot 80 and eventually engages the triangular projection 80A. The tapered shape of the leading edge portion 70B allows each arm 68 to be resiliently deflected by a small amount in a radially outward direction with respect to the longitudinal axis LA of the needle 14. As the threaded member 60 continues to be rotated, each triangular recess 70A is eventually brought into registration with the corresponding triangular projection 80A. The resilience of the material of the arms 74 forces the recesses 70A down onto the triangular projections 80A so that the projections are partially received in the recesses to retain the connection. The technician will experience a tactile or audible snap as a result of this registering event that confirms the threaded member 60 is secured in place. By applying sufficient torque in the direction of arrow A3, the fingers 76 can rotate to move the triangular recesses 70A off of the triangular projections 80A through deflection of the arms 78. It will be understood that the shape of a projection and recess may be other than triangular. Moreover, the projection could be on a finger and a recess could be in a slot of a handle. Still further, the retention feature could be omitted within the scope of the invention.

To release the threaded member 60, and hence the depth stop unit 50 from connection with the distal handle member 24, the connector 66 (and hence the entire threaded member 60) is rotated about 90 degrees in the direction indicated by arrow A3 from its connected position shown in FIG. 1 to a release position shown in FIG. 2. Rotation of the connector 66 moves the fingers 70 out of the slots 80 so that the depth stop unit 50 is no longer connected to the distal handle member 24. The connection may be described as "bayonet". However, it will be understood that other types of connections, including non-rotary connections may be used within the scope of the present invention. Generally speaking, a quick release connection is desirable (but not mandatory in the present invention). For rotary connections, it is desirable to release connection with less than a 360 degree turn of the connector and more desirable to require a turn of less than 180 degrees to release connection. The bayonet connection illustrated in the drawings requires only about a 90 degree turn to achieve both connection and disconnection. Connection can be made by turning the connector 66 of the threaded member 60 from the position in FIG. 2 back to the position of FIG. 1.

Once the threaded member 60 is disconnected from the distal handle member 24 by this motion, the depth stop unit 50 can freely slide down the needle 14 and off of its distal end so that the depth stop unit is entirely removed from the needle assembly 10, as is illustrated in FIG. 3. The entire length of the needle 14 projecting outwardly from the tubular portion 82 is now available for penetrating into the body of the patient to the target bone. If desired, the depth stop unit 50 can be reattached to the needle 14 because the disconnection is non-destructive.

Generally circumferentially extending ribs 88 are located on the depth stop 52 at the intersection of the conical portion 54 and the cylindrical portion 56. It will be understood that ribs (not shown) could be placed at other locations, such as on the arms 68 of the threaded member 60. The ribs 88 are spaced apart axially of each other along the longitudinal axis of the threaded member 60. The wave shape of the ribs 88 suggests by its circumferential extent that removal of the depth stop unit 50 requires rotary motion about the axis of the threaded member 60 and needle 14. The axial extent of the ribs 88 suggests a second movement along the axis is needed. These provide indications to the medical technician of how to release the depth stop unit 50 and then slide it off of the needle assembly.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "up", "down", "top" and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A convertible needle assembly comprising:
   a mounting structure;
   a needle having a longitudinal axis and a sharp end, the needle being mounted on the mounting structure and projecting from the mounting structure so that the sharp end is generally remote from the mounting structure;
   a depth stop adapted to limit the depth of penetration of the needle;
   a rotary connector adapted to releasably connect the depth stop to the needle assembly, the released depth stop being removable from the needle for increasing the possible depth of penetration of the needle,
   wherein the mounting structure comprises a pair of slots and the rotary connector comprises a pair of fingers constructed and arranged to be received in the slots, and the rotary connector and mounting structure are constructed for bayonet connection of the rotary connector to the mounting structure, the slots extending circumferentially around the mounting structure, each slot being open on one circumferential end and closed on another circumferential end such that rotation of the rotary connector moves the fingers out of the slots to disconnect the rotary connector from the mounting structure;
   wherein the rotary connector is constructed and arranged to connect to the mounting structure by making a turn in a first direction about an axis that is less than 360 degrees, and to release from the mounting structure by making a turn in a second direction opposite the first direction about the axis that is less than 360 degrees;
   wherein said pair of fingers are fingers which project inwardly from respective arms, each finger has a tapered leading edge portion allowing each arm to be resiliently deflected in a radially outward direction with respect to the longitudinal axis of the needle; and
   wherein the mounting structure comprises a handle, the needle assembly further comprising a depth stop unit comprising a positioning stem, the depth stop mounted on the positioning stem and movable along a length of the stem to different selected positions along the stem and along the longitudinal axis of the needle, the depth stop having a stop surface adapted to limit the depth of penetration of the needle, and wherein the rotary connector is constructed and arranged to releasably connect the stem to the needle assembly wherein the slots and fingers include retention structures to resist relative rotation between the rotary connector and the handle, the retention structures comprising a triangular projection located in the slot and a triangular recess located on the finger, the triangular projection being adapted to snap into the triangular recess to provide a tactile confirmation of engagement.

2. A convertible needle assembly as set forth in claim 1 wherein the rotary connector is constructed and arranged to connect to the mounting structure and release from the mounting structure by making turns in the first and second directions, respectively, that are less than 180 degrees.

3. A convertible needle assembly as set forth in claim 1 wherein the rotary connector is constructed and arranged to connect to the mounting structure and release from the mounting structure by making turns in the first and second directions, respectively, that are about 90 degrees.

4. A convertible needle assembly as set forth in claim 1 wherein the rotary connector mounts the depth stop for selective positioning along the length of the needle to change the depth limit of penetration.

5. A convertible needle assembly as set forth in claim 1 wherein the stem is elongate and has threads along its length, the depth stop having threads mated with the threads of the rotary connector and being rotatable on the rotary connector for selective positioning along the length of the needle.

6. A convertible needle assembly as set forth in claim 5 wherein the rotary connector and depth stop are conjointly removable from the needle.

7. A convertible needle assembly as set forth in claim 1 wherein the rotary connector and positioning stem are formed as one piece.

8. A convertible needle assembly as set forth in claim 1 wherein the positioning stem is elongate and has threads along its length, the depth stop having threads mated with the threads of the positioning stem and being rotatable on the positioning stem for selective positioning along the length of the needle.

9. A convertible needle assembly as set forth in claim 1 wherein the depth stop has an axially extending passage extending through an entire length of the depth stop, the passage including a larger diameter portion at a top end of the depth stop and a smaller diameter portion at a bottom end.

10. A convertible needle assembly as set forth in claim 1 wherein the depth stop include a conical portion and a cylindrical nose portion extending proximally from the conical portion.

* * * * *